United States Patent [19]
Osterlind

[11] Patent Number: 5,846,227
[45] Date of Patent: Dec. 8, 1998

[54] MEDICAL DEVICES

[75] Inventor: Roland J. Osterlind, Hoeganaes, Sweden

[73] Assignee: The BOC Group plc, Windlesham, England

[21] Appl. No.: 662,737

[22] Filed: Jun. 10, 1996

[51] Int. Cl.⁶ .................................................. A61M 5/00
[52] U.S. Cl. .................... 604/164; 604/198; 604/264
[58] Field of Search .................................. 604/164, 165, 604/167, 168, 171, 195, 240, 198, 272, 263, 264

[56] References Cited

U.S. PATENT DOCUMENTS

| | | | |
|---|---|---|---|
| 5,000,736 | 3/1991 | Kaufhold, Jr. et al. | 604/195 X |
| 5,057,086 | 10/1991 | Dillard, III et al. | 604/195 |
| 5,205,829 | 4/1993 | Lituchy | 604/164 |
| 5,263,934 | 11/1993 | Haak | 604/195 X |
| 5,312,359 | 5/1994 | Wallace | 604/164 |
| 5,456,668 | 10/1995 | Ogle, II | 604/195 X |

*Primary Examiner*—John D. Yasko
*Attorney, Agent, or Firm*—Rogert M. Rathbun; Salvatore P. Pace

[57] ABSTRACT

A catheter assembly includes a hollow needle having a sharpened distal tip which is movable between a position in which the needle is located within a housing and a patient penetrating position in which the distal tip extends beyond the distal end of a catheter. The catheter and a catheter hub form a catheter assembly which is supported on a catheter hub support.

The catheter hub support is a one-piece molding and includes a gaskets and means that wipe the outside of the needle when the needle is withdrawn from the patient back within the housing to a needle protected position. The function of gasket means is to retard the flow of blood between the catheter hub and the catheter hub support.

3 Claims, 4 Drawing Sheets

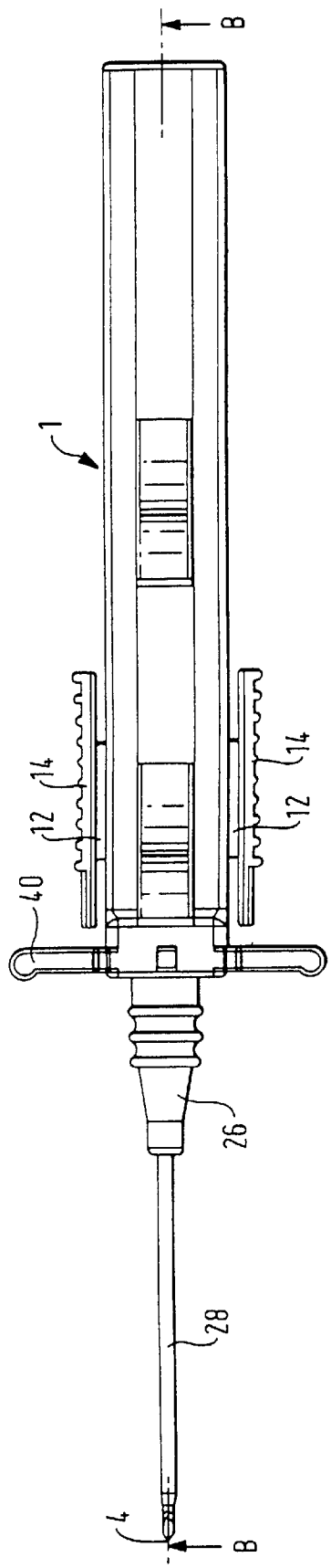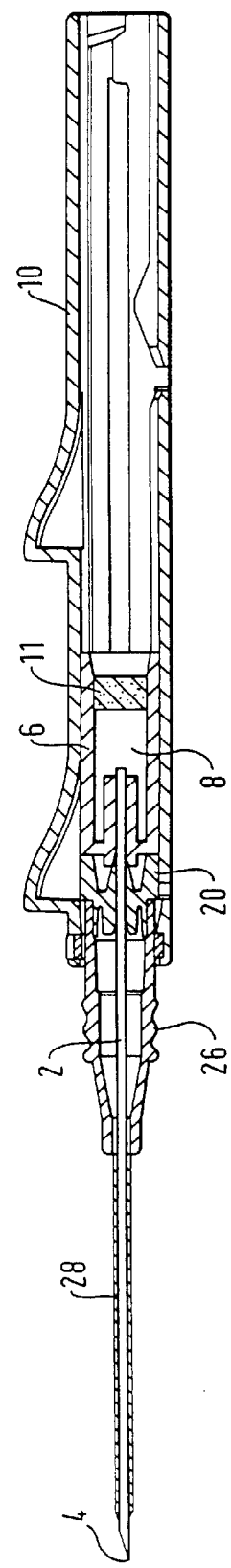
FIG. 3
FIG. 4

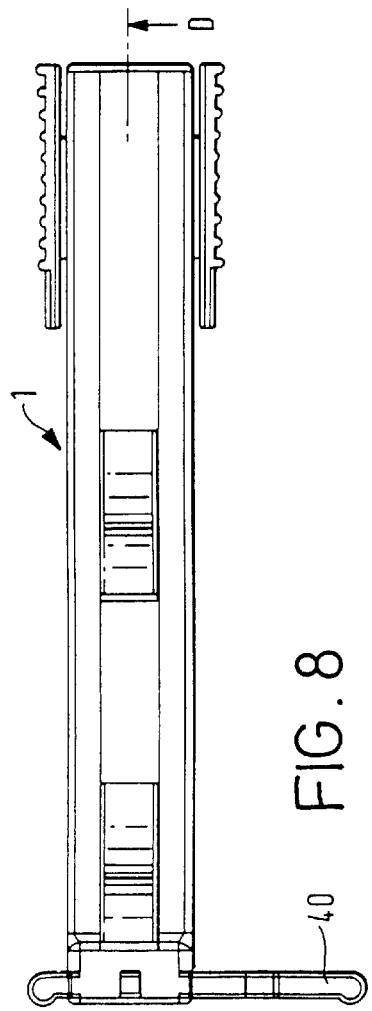
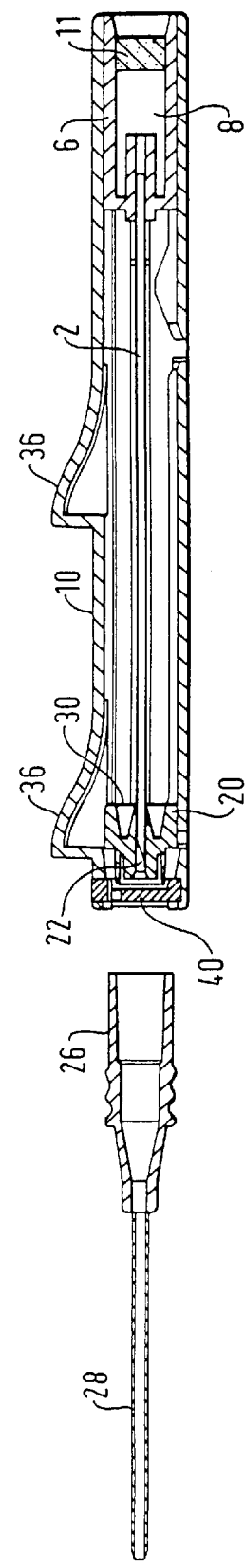

ic devices and, in particular, to medical devices such as intravenous catheters which include a hollow needle having a sharp distal end for piercing the skin of a patient.

MEDICAL DEVICES

BACKGROUND OF THE INVENTION

The present invention relates to medical devices and, in particular, to medical devices such as intravenous catheters which include a hollow needle having a sharp distal end for piercing the skin of a patient.

The existence of infectious diseases such as AIDS and Hepatitis has highlighted the danger to which medical personnel may be exposed when treating patients by means of catheter devices where a sharp needle point is used to pierce the skin of a patient. Medical personnel have been infected by physical contact with or accidental prick by an infected needle (needle-stick).

Not only is it desirable to protect medical personnel from the dangers of inadvertent needle-stick, but it is also desirable to provide protection from any other contact with the patients blood.

A known device for protecting a needle both before and after use is described in European Patent Publication No. 0599564, in which a needle is arranged within a housing and is displaceable between a retracted position and a second extended position. Means is provided for displacing the needle between said first and second positions. A sealing means for sealing the initial open distal end of the housing is connected to the displacing means, at least initially. The sealing means during displacement of the needle from said first retracted position to said second position, is moved in the direction towards the open distal end of the housing to a sealing position and is then fixed in said sealing position substantially sealing the interior of the housing. The sealing means includes a plug eg. of cellular plastics material so that when the needle is retracted back into the retracted position within the housing, the needle passes through the plug which will wipe the needle so that fluids such as blood, adhering to the needle will be absorbed by the plug and start swelling so as to finally seal the sealing means. As a result, the needle is essentially free from adhering fluid and there is no risk of fluid dripping into the interior of the housing.

The utilisation of the seal and a plug each separately manufactured and assembled together renders the cost of manufacture expensive.

European Patent Publication No. 0408290 describes means for protecting medical personnel against contact with a patient's blood due to leakage of blood from a catheter which includes forming a gasket in situ at the open distal end of a nose portion of a needle guard upon which nose portion a hub part of a catheter is supported.

The formed-in-place gasket allows the needle guard to slide smoothly along the needle and prevents the back flow of blood into the needle guard through the annular gap between the outside surface of the needle and the inside surface of the catheter.

This solution is somewhat complicated by having to form the gasket in situ which increases the cost of producing the catheter assembly.

It is an aim of the present invention to provide a simple and cost-effective means to retard the flow of blood through a support or a catheter hub forming part of a medical device such as an intravenous catheter.

SUMMARY OF THE INVENTION

According to the present invention, a catheter assembly comprises a hollow needle having a sharpened distal end for piercing the skin of a patient, means for moving the needle longitudinally relative to a housing, said moving means being employed to retract the needle after use back within the housing to a needle protected position, a catheter hub support having an aperture for the passage therethrough of the needle, and sealing means for retarding the flow of blood into the housing; in which the catheter hub support and the sealing means are formed as an integral one-piece molding.

The sealing means is preferably formed at the proximal end of the catheter hub support and a further sealing means is formed at the distal end of the catheter hub support.

Preferably, the catheter hub support is located completely within the housing adjacent an open distal end thereof.

BRIEF DESCRIPTION OF THE DRAWINGS

An embodiment of the invention will now be described by way of example, reference being made to the Figures. of the accompanying diagrammatic drawing in which:

FIG. 3 is a plan view of the catheter assembly of FIG. 1 but with various parts in a patient penetrating position;

FIG. 4 is a cross-section on the line BB of FIG. 3;

FIG. 8 is a plan view of a cannula assembly separated from the remainder of the catheter assembly of FIG. 1; and FIG. 9 is a cross-section on the line DD of FIG. 8.

Figure 1:
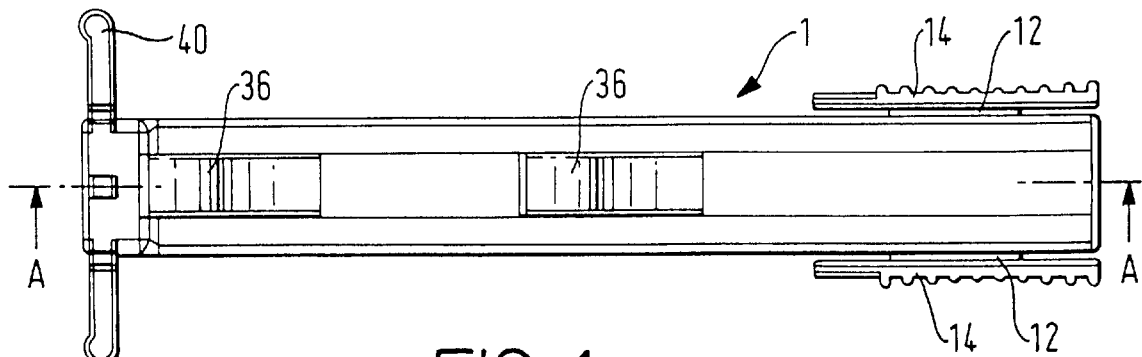
FIG. 1 is a plan view of an i.v catheter assembly prior to use.

As shown, a catheter assembly 1 includes a hollow needle 2 having a sharpened distal end 4. The proximal end of the needle 2 is fixably mounted in a hollow needle hub 6 which defines a flash chamber 8. The proximal end of the flash chamber 8 is closed by a porous plug 11. The needle hub 6 is located for sliding movement within a housing 10. Webs 12 extend from each side of the needle hub 6 through slots (not shown) in the housing 10 to support serrated grippers 14 in a manner known per se.

It will be evident that the user will engage the grippers 14 when seeking to move the needle 2 and the needle hub 6 longitudinally along the interior of the housing 10 as will be explained.

Figure 2:
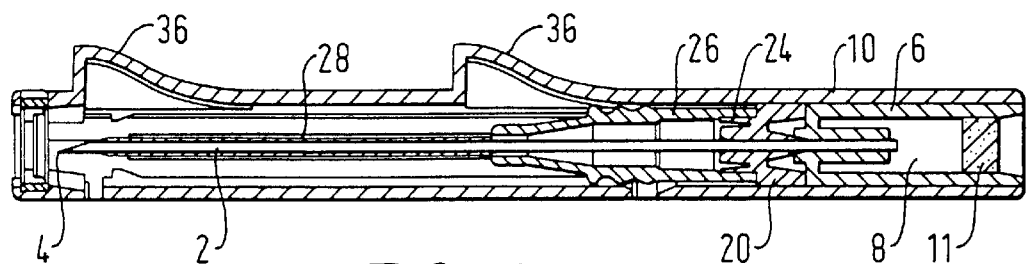
FIG. 2 is a cross-section on the line AA of FIG. 1.

As shown in FIG. 2 in the ready for use position, a catheter hub support 20 formed with a central aperture 22 is located immediately forward of the needle hub 6 for forward movement therewith. As shown the needle 2 passes through the aperture 22. An annular forward facing flange 24 on the hub support 20 supports a catheter hub 26 forming part of an assembly including a hollow catheter 28.

Figure 7:
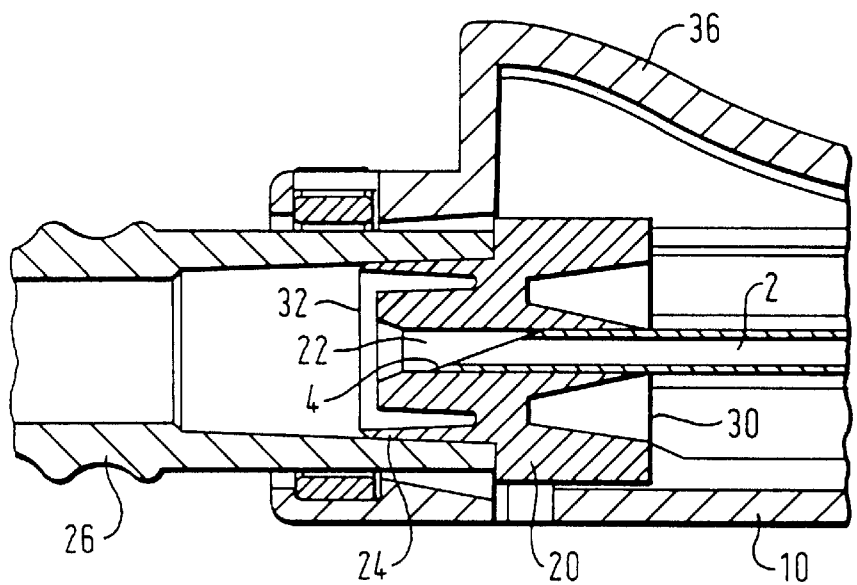
FIG. 7 is an enlarged cross-sectional detail including a catheter hub support and sealing means forming part of the catheter assembly with parts in the needle protection position as shown in FIG. 6.

The catheter hub support 20 is a one-piece molding (see in particular FIG. 7) and includes a first sealing means in the form of a gasket 30 located at the proximal end of the hub support 20 and a second sealing means in the form of a gasket 32 located at the free end of the flange 24.

Figure 5:
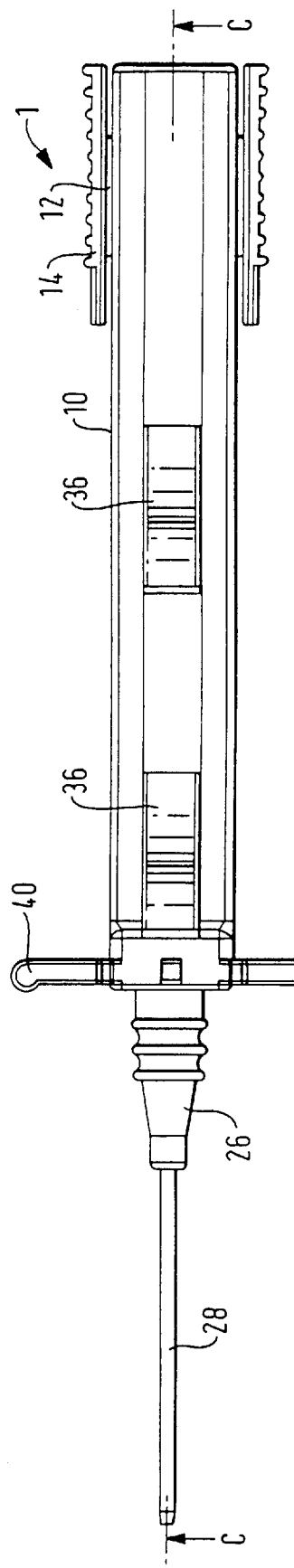
FIG. 5 is a plan view of the catheter assembly of FIG. 1 but with various parts illustrated in a needle protection position after the needle has been withdrawn from a patient.

The distal end of the housing 10 is open, but a door 40 is mounted for sliding movement on the distal end of the housing 10 for movement between a first position illustrated in FIGS. 8 and 9 in which it blocks any movement of the needle 2 out from the housing 10 and a second position illustrated in FIGS. 1, 3 and 5, in which a hole in the door is aligned with the open distal end of the housing 10 to permit movement of the needle 2 to and from the interior of the housing 10.

The disposition of the door on the housing 10 is described more fully in our European patent Application No. 96.300115.1.

Protuberances 36 are formed on the upper (as shown) surface of the housing 10 in a manner known per se.

In the ready-for-use position as illustrated in FIGS. 1 and 2, the needle 2 is located completely within the housing 10 with the needle hub 6 and hence the grippers 14 located adjacent the proximal end of the housing 10. The door is in its second position in which a hole in said door 40 is aligned with the open distal end of the housing 10.

To displace the needle 2 from the ready for use position illustrated in FIGS. 1 and 2 to a patient penetrating position illustrated in FIGS. 3 and 4, the grippers 14 are engaged and move the needle hub 6, catheter hub support 20 together with the needle 2 and the catheter hub 26 and catheter 28 along the interior of the housing 10 in a manner known per se. Movement of the grippers 14 is limited by the engagement of the hub-support 20 against the distal end of the housing 10 where said hub-support is fixed in a manner known per se (see European Patent Publication No 0599564). The dimensions of the needle 2 and the catheter 28 are such that in the ready to pierce position the sharpened distal end 4 of the needle 2 will extend shortly from the open free end of the catheter 28 in a manner known per se.

Figure 6:
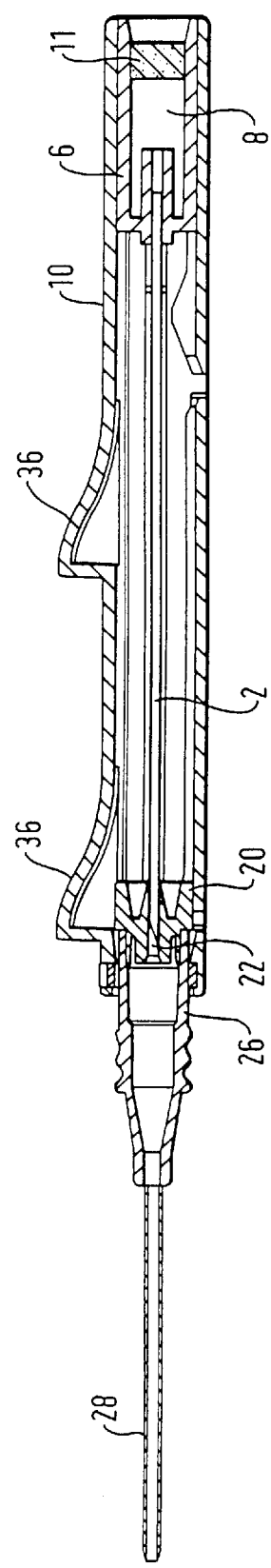
FIG. 6 is a cross-section on the line CC of FIG. 5.

Once penetration of the skin of a patient has been effected and the distal end of the catheter 28 positioned within the vein of a patient; the grippers 14 are engaged to withdraw the needle 2 through the catheter 28 and catheter hub 26 back into the interior of the housing 10 to the position illustrated in FIGS. 5 and 6. It will be evident that as the needle 2 passes back along the aperture 22 of the hub support 20 the gasket 30 will effectively wipe the outside of the needle 2 and retard the flow of blood into the interior of the housing 10.

The function of the gasket 32 is to retard the flow of blood between the catheter hub 26 and the hub support 20.

Once the needle end 4 is safely located within the aperture 22 of the catheter hub support 20 which remains adjacent but entirely within the forward distal end of the housing 10, then the catheter hub 26 can be released from the support 20 (see FIGS. 8 and 9) without any danger of medical personnel inadvertently touching the distal end of the catheter hub support 20 which might be contaminated with the patient's blood. After the catheter hub 26 is released from the support 20 the door 40 is moved to its first position in which movement of the needle 2 out from the distal end of the housing 10 is effectively blocked.

As is known, there is always the possibility of blood travelling along the annular gap between the outside surface of the needle 2 and the inside surface of the catheter 28 but by positioning the catheter hub support 20 completely within the housing 10 at a distance from the open distal end of the housing 10, then accidental contact by a user of the catheter assembly is substantially avoided.

In the above described embodiment, since the distal end of the hub support 20 is displaced within the housing 10 away from the open distal end of the housing 10, then it is substantially impossible for a user to touch the distal end of the hub support 20. This feature for containing the hub support 20 entirely within the housing 10 means that the user of the catheter assembly cannot inadvertently come into contact with any blood on the hub support 20 when the catheter hub 26 is disconnected from the hub support 20.

I claim:

1. A catheter assembly comprising a hollow needle having a sharpened distal end for piercing the skin of a patient, a housing having a distal end, means for moving said needle longitudinally relative to said housing between a first, extended position wherein said needle extends outwardly with respect to said distal end of said housing and a second, retracted position wherein said needle is contained within said housing, a catheter hub support having an aperture for the passage therethrough of the needle, said catheter hub support being movable with said needle as said needle moves to said first, extended position to be retained in position at the distal end of said housing and sealing means for retarding the flow of blood into said distal end of said housing, in which said catheter hub support and said sealing means are formed as an integral one piece molding.

2. A catheter assembly as claimed in claim 1 in which the sealing means is formed at the proximal end of the catheter hub support and a further sealing means is formed at the distal end of the catheter hub support.

3. A catheter hub assembly as claimed in claim 1 in which the catheter hub support is located completely within the housing adjacent an open distal end thereof.

* * * * *